United States Patent
Williams

(10) Patent No.: US 7,094,051 B2
(45) Date of Patent: *Aug. 22, 2006

(54) ORTHODONTIC APPLIANCE

(76) Inventor: Michael O. Williams, 58 Shoreline La., Gulfport, MS (US) 39053

( * ) Notice: Subject to any disclaimer, the term of this patent is extended or adjusted under 35 U.S.C. 154(b) by 306 days.

This patent is subject to a terminal disclaimer.

(21) Appl. No.: 10/439,638

(22) Filed: May 16, 2003

(65) Prior Publication Data

US 2003/0194675 A1 Oct. 16, 2003

Related U.S. Application Data

(63) Continuation-in-part of application No. 10/186,604, filed on Jul. 2, 2002, now Pat. No. 6,877,982, which is a continuation-in-part of application No. 09/975,633, filed on Oct. 12, 2001, now Pat. No. 6,719,557, which is a continuation-in-part of application No. 09/750,527, filed on Dec. 29, 2000, now Pat. No. 6,520,772, which is a continuation-in-part of application No. 09/598,766, filed on Jun. 22, 2000, now Pat. No. 6,402,510, which is a continuation-in-part of application No. 09/406,426, filed on Sep. 27, 1999, now Pat. No. 6,241,517, which is a continuation-in-part of application No. 09/143,071, filed on Aug. 28, 1998, now Pat. No. 6,036,488, which is a continuation-in-part of application No. 09/065,344, filed on Apr. 23, 1998, now Pat. No. 5,919,042.

(51) Int. Cl.
A61C 3/00 (2006.01)

(52) U.S. Cl. ............................................. 433/7; 433/18
(58) Field of Classification Search .............. 433/6–7, 433/18–19, 21, 24
See application file for complete search history.

(56) References Cited

U.S. PATENT DOCUMENTS

| | | | |
|---|---|---|---|
| 4,713,000 A * | 12/1987 | Rosenberg | 433/18 |
| 4,723,910 A * | 2/1988 | Keller | 433/7 |
| 5,064,370 A * | 11/1991 | Jones | 433/21 |
| 5,439,377 A * | 8/1995 | Milanovich | 433/7 |
| 5,505,616 A * | 4/1996 | Harwell | 433/21 |
| 5,645,422 A | 7/1997 | Williams | |
| 5,769,631 A | 6/1998 | Williams | |
| 5,919,042 A | 7/1999 | Williams | |
| 6,036,488 A | 3/2000 | Williams | |
| 6,241,517 B1 | 6/2001 | Williams | |
| 6,402,510 B1 | 6/2002 | Williams | |
| 2002/0025502 A1 | 2/2002 | Williams | |
| 2002/0172909 A1 | 11/2002 | Williams | |

* cited by examiner

*Primary Examiner*—John J Wilson
(74) *Attorney, Agent, or Firm*—Paul M. Denk

(57) ABSTRACT

A mandibular and maxillary arch expansion apparatus having a first and second forward orthodontic bands and first and second rear orthodontic bands. The respective forward and rear orthodontic bands are interconnected by an expansion sheath element. The two forward bands are connected by a substantially straight, solid rod. The expansion sheaths exert lengthening forces while the solid rod resists lateral or widening forces. Also provided is a maxillary apparatus connected to a mandibular apparatus by a telescoping contraction connector. The device is positioned to exert adjustable contracting pressure for the correction of Class II malocclusions or overbite. Also provided is an arch expansion apparatus with a centrally disposed expansion element having two forward connector wires extending outwardly therefrom and two rearward connector wires extending outwardly. Each connector wire has an orthodontic band on the terminal end. The expansion element can be actuated so as to elongate the expansion element so as to exert arch expansion pressure.

4 Claims, 7 Drawing Sheets

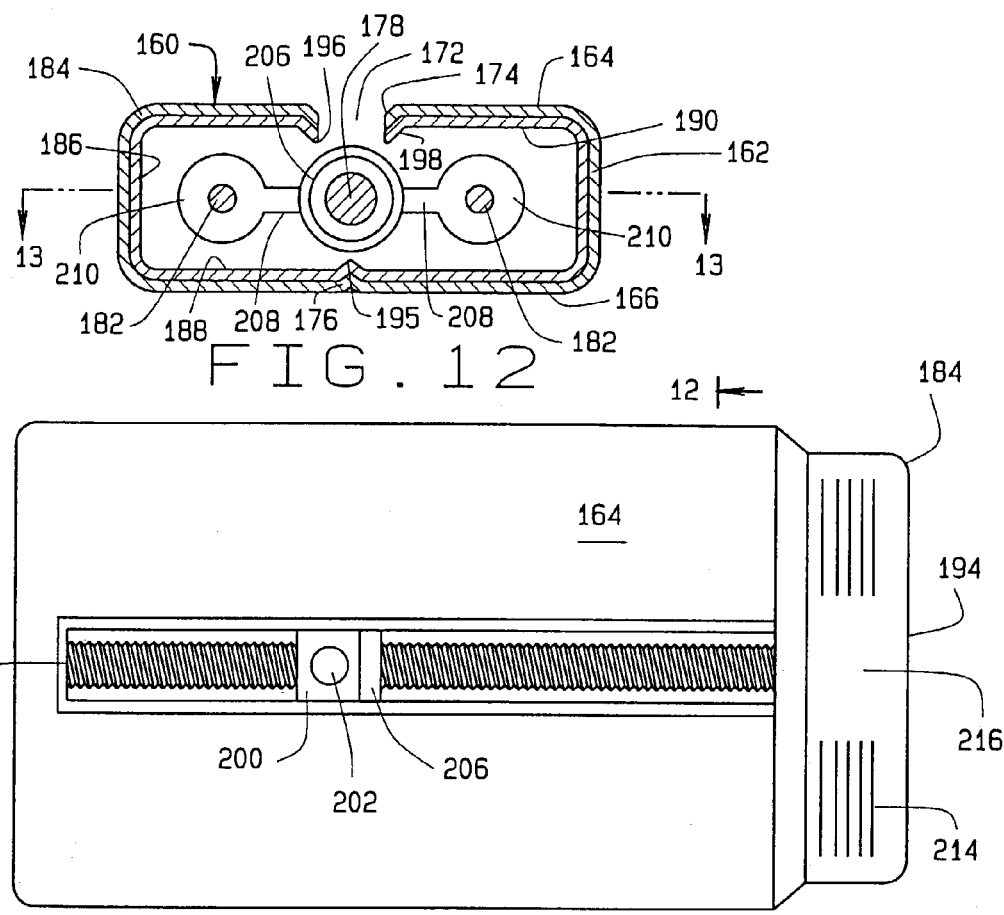
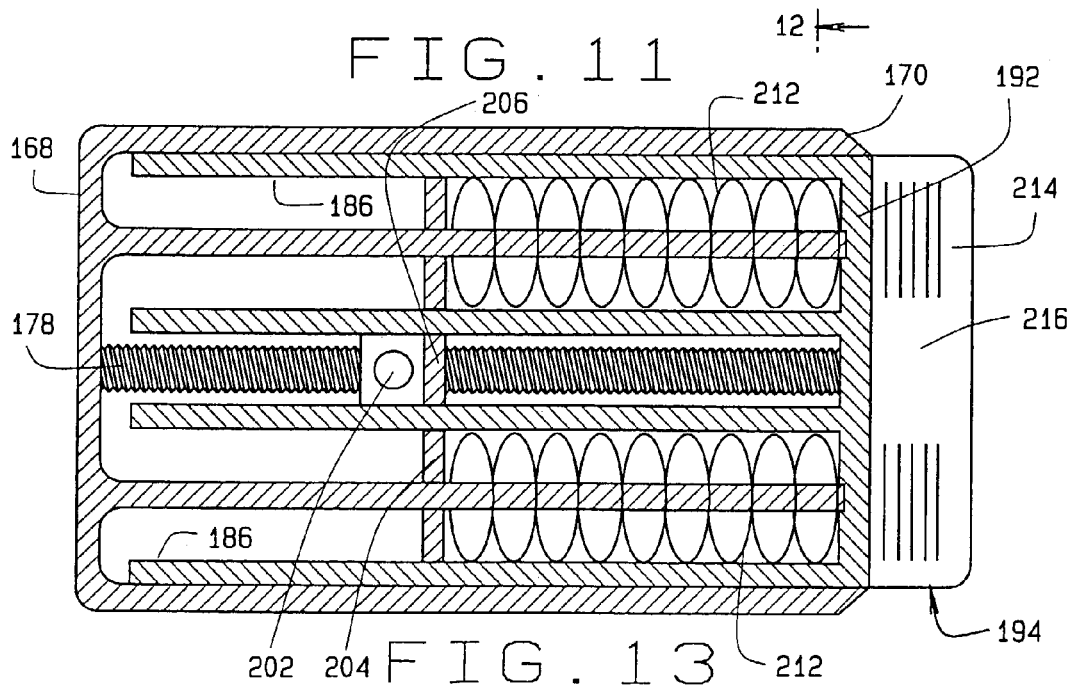

ORTHODONTIC APPLIANCE

CROSS-REFERENCE TO RELATED APPLICATIONS

This application is a continuation-in-part of application Ser. No. 10/186,604, filed Jul. 2, 2002, now U.S. Pat. No. 6,877,982, which is a continuation-in-part of application Ser. No. 09/975,633, filed Oct. 12, 2001, now U.S. Pat. No. 6,719,557, and this application is a continuation-in-part of application Ser. No. 09/750,527, filed Dec. 29, 2000, now U.S. Pat. No. 6,520,772, which is a continuation-in-part of application Ser. No. 09/598,766, filed Jun. 22, 2000, now U.S. Pat. No. 6,402,510, which is a continuation-in-part of application Ser. No. 09/406,426, filed Sep. 27, 1999, now U.S. Pat. No. 6,241,517, which is a continuation-in-part of application Ser. No. 09/143,071, filed Aug. 28, 1998, now U.S. Pat. No. 6,036,488, which, in turn, is a continuation-in-part of application Ser. No. 09/065,344, filed Apr. 23, 1998, now U.S. Pat. No. 5,919,042, which is related to application Ser. No. 08/526,686, filed Sep. 11, 1996, now U.S. Pat. No. 5,645,422, and related to Ser. No. 08/688,110, filed Jul. 29, 1996, now U.S. Pat. No. 5,769,631, all of which are incorporated herein by reference.

STATEMENT REGARDING FEDERALLY SPONSORED RESEARCH OR DEVELOPMENT

Not Applicable.

BACKGROUND OF THE INVENTION

This invention relates generally to orthodontic devices and, in particular, to improved devices for expanding maxillary and mandibular arches and devices for treating an overbite and related malocclusions.

SUMMARY OF THE INVENTION

One aspect of the invention provides for a maxillary arch expander that provides lengthening forces but resists lateral expansion;

Another aspect of the invention provides for a mandibular arch expander that provides lengthening forces but resists lateral expansion;

Another aspect of the invention provides for a device for correction of Class II overbite;

Yet another aspect of the invention provides for an orthodontic arch expander that includes a centrally disposed expansion apparatus operatively connected to orthodontic bands by wires.

These and other aspects of the invention are provided in the described and illustrated embodiments of the present invention. According to the invention, briefly stated, a mandibular and maxillary arch expansion apparatus is provided having a first and second forward orthodontic bands and first and second rear orthodontic bands. The respective forward and rear orthodontic bands are interconnected by an expansion sheath element. The two forward bands are connected by a substantially straight, solid rod. The expansion sheaths exert lengthening forces while the solid rod resists lateral or widening forces.

Another embodiment of the invention provides for a maxillary apparatus connected to a mandibular apparatus by a telescoping contraction connector. The device is positioned to exert adjustable contracting pressure for the correction of Class II malocclusions or overbite.

Another embodiment of the invention provides an orthodontic arch expander having centrally disposed expansion element. The expansion element includes two forward connector wires extending outwardly therefrom and two rearward connector wires extending outwardly. Each connector wire has an orthodontic band on the terminal end. The orthodontic bands are attached to the appropriate teeth. The expansion element can be actuated so as to elongate the expansion element so as to exert arch expansion pressure.

BRIEF DESCRIPTION OF THE DRAWINGS

FIG. 11 is a plan view of the expansion element of the arch expander of FIG. 10;

FIG. 12 is a cross-section view of the expansion element of the arch expander taken along line 12—12 of FIG. 11;

FIG. 13 is a cross-sectional view of the expansion element of taken along line 13—13 of FIG. 12;

DESCRIPTION OF THE PREFERRED EMBODIMENT

Figure 1:
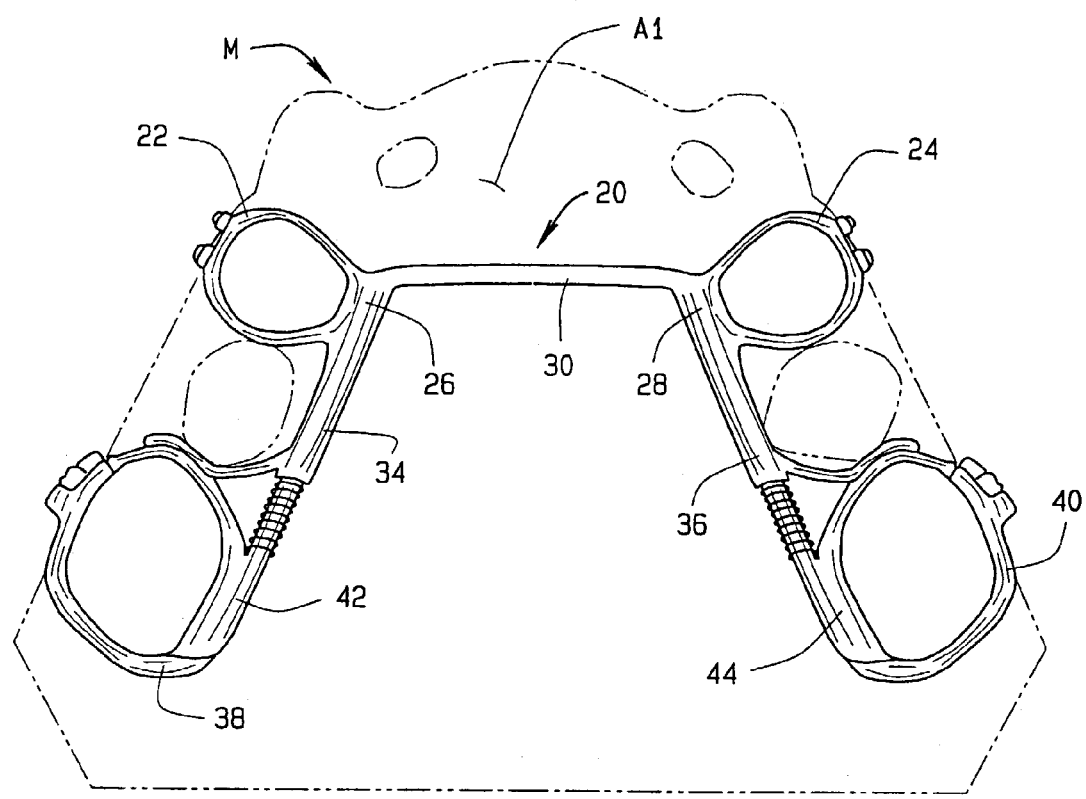
FIG. 1 is a perspective view of an orthodontic appliance of the present invention attached to a mold of the maxillary arch.
Figure 2:
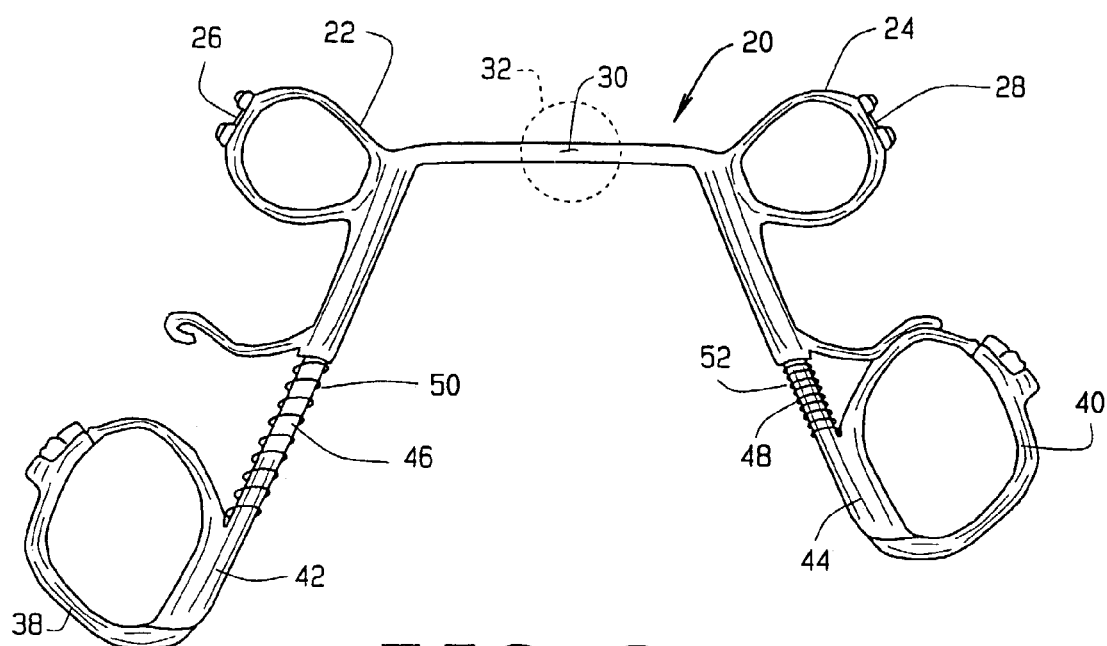
FIG. 2 is another perspective view of the orthodontic appliance of FIG. 1.

Referring now to the drawings, FIGS. 1 and 2 illustrate a maxillary arch expansion appliance, indicated generally by reference numeral 20 attached to a maxillary mold M. Appliance 20 includes a pair of spaced apart forward orthodontic bands 22 and 24 including bosses 26 and 28 integrally formed thereon. The bosses are positioned on the lingual side of the bands. There is a connecting rod 30 between the forward bands, generally attached to the bosses.

The rod can be a separate element or integrally formed with the bosses and bands. In any event, rod 30 is a substantially straight, rigid element that maintains a desired distance between the forward bands and the length of rod 30 is dictated by the width of the maxillary arch. The rod 30 can have a generally centrally positioned piece of acrylic or nance button 32 that is molded to conform to the contour of the subject's maxillary arch A1.

There is a first hollow tube 34 extending from boss 26 and a second hollow tube 36 extending from boss 28. The angles at which the respective tubes extend from the bosses depend upon the morphology of the arch A1. Apparatus 20 also includes a pair of spaced apart rear orthodontic bands 38 and 40. The rear bands include respective bosses 42 and 44. A rod 46 is integrally connected to boss 42 and a rod 48 is integrally connected to boss 44. Rods 46 and 48 are sized and dimensioned to seat in hollow tubes 34 and 36, respectively, in a sliding relationship. There is a coil spring 50 around rod 46 and a coil spring 52 around rod 48. The springs are sized to abut the hollow tubes that are integral with the forward bands. It will be noted that in device 20, intended for use in the maxillary arch, the recited springs are positioned around rods integral with the rear orthodontic bands and the springs are thus adjacent and abut the rear bands. The recited springs urge the forward bands away from the rear bands and have a predetermined force to be delivered between the teeth to distalize the maxillary molars while rod 30 resists and lateral or widening effect.

Figure 3:
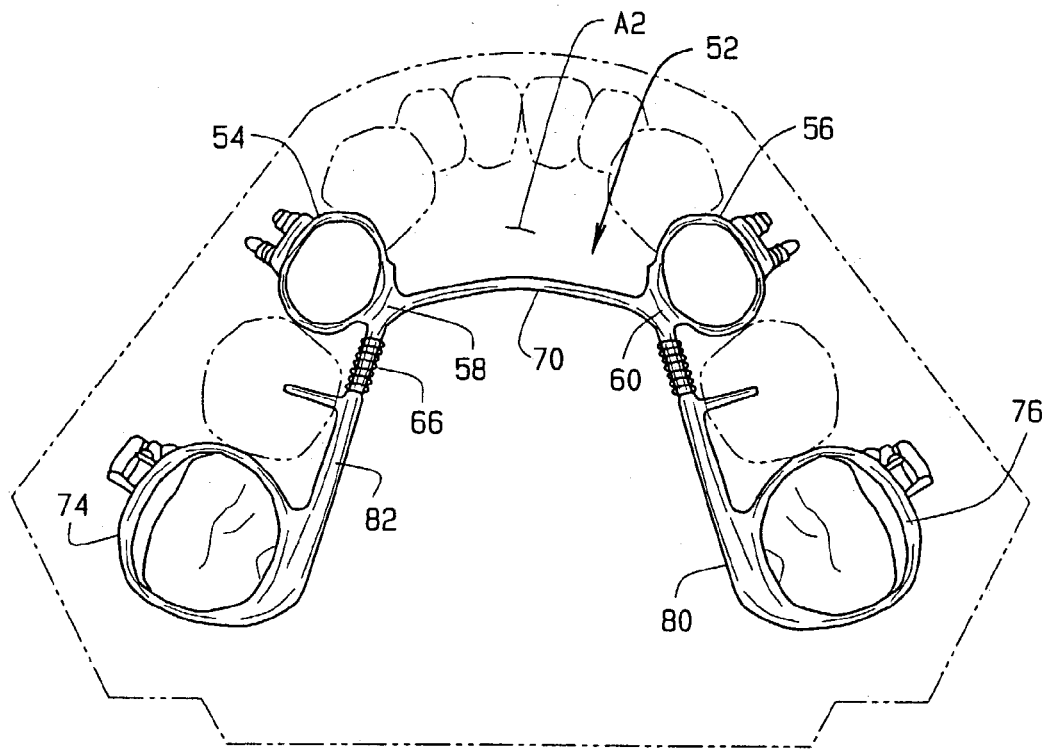
FIG. 3 is a perspective view of an orthodontic appliance of the present invention attached to a mold of the mandibular arch.
Figure 4:
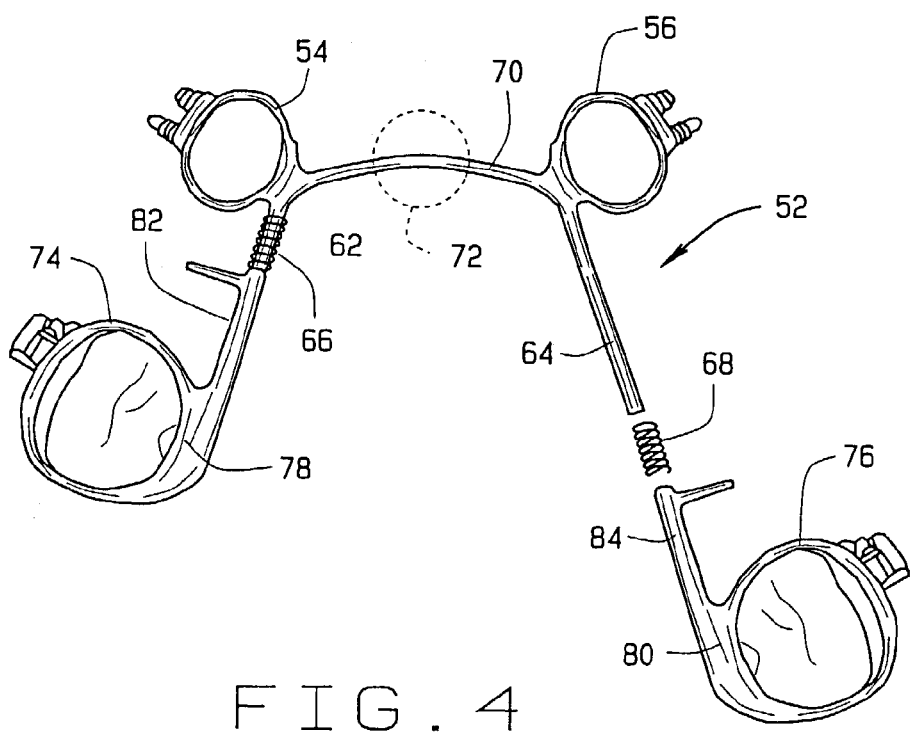
FIG. 4 is another perspective view of the mandibular orthodontic appliance of FIG. 3, the left spring-loaded tube assembly disassembled.
Figure 5:
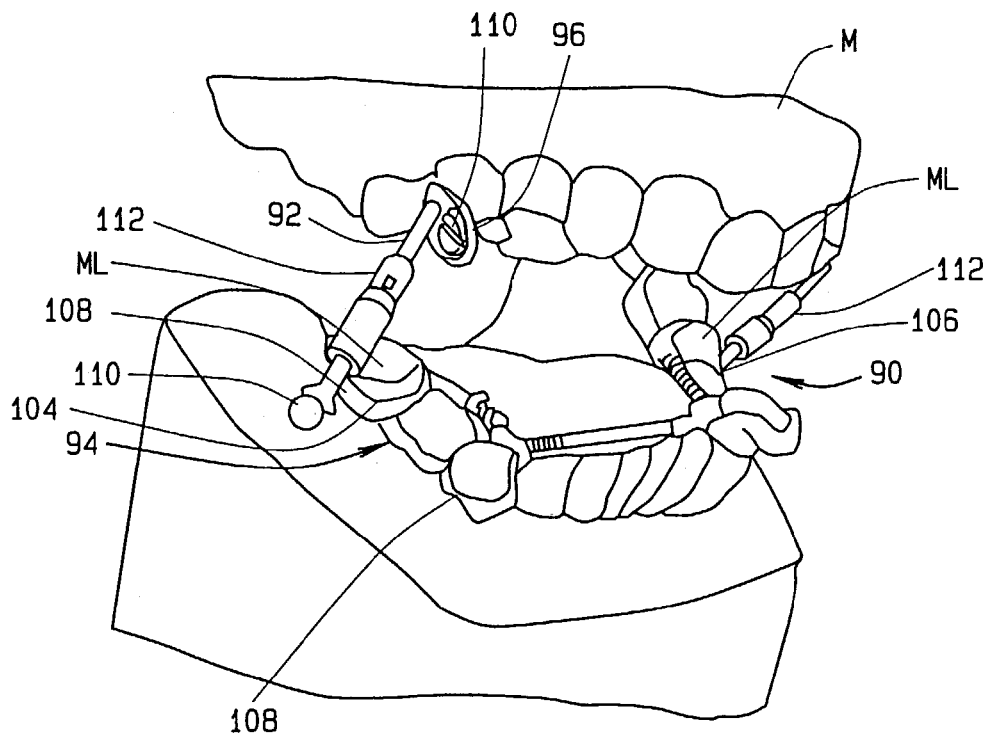
FIG. 5 is a perspective view of another embodiment of a mandibular apparatus and maxillary arch apparatus for correction of Class II overbite which are shown mounted in a mold and connected by a telescoping assembly.
Figure 6:
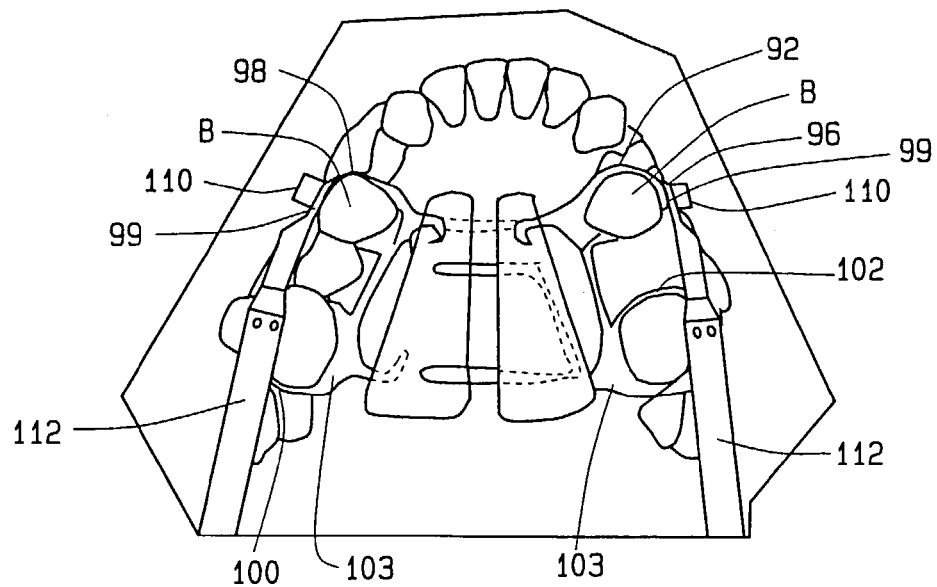
FIG. 6 is a bottom plan view of the maxillary arch apparatus of FIG. 4 mounted in the mold with the telescoping assembly mounted thereto.
Figure 7:
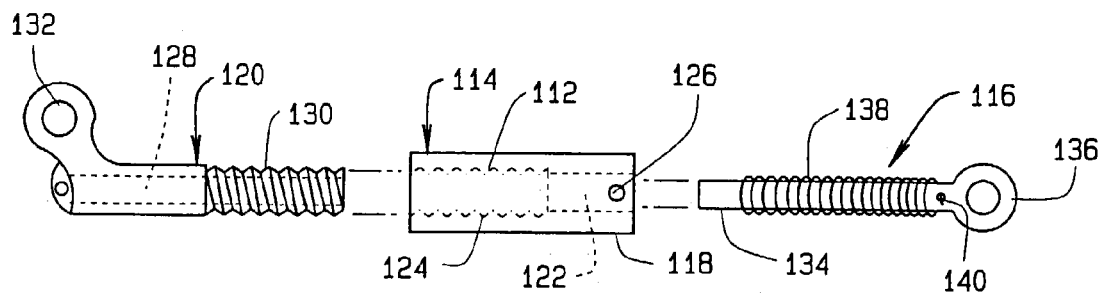
FIG. 7 is an exploded view of a contraction sheath connector for connecting a maxillary arch apparatus to a mandibular arch apparatus in the correction of Class II overbite.

FIGS. 3 and 4 illustrate a mandibular arch expansion device indicated generally by reference numeral 52 Appliance 52 includes a pair of spaced apart forward orthodontic bands 54 and 56 having integral bosses 58 and 60, respectively. A first rod 62 extends from boss 58 and a second rod 64 extends from boss 60. The angles at which the rods extend outwardly from the bosses depend upon the morphology of the mandibular arch A2. There is a first coil spring 66 around rod 62 and a second coil spring 68 around rod 64. The forward bands are interconnected by a substantially straight and relatively rigid rod 70. The rod can be embedded in an acrylic button, as at 72.

Apparatus 52 also includes a first rear orthodontic band 74 and a second orthodontic band 76 and respective integral bosses 78 and 80. A first hollow tube 82 extends from boss 78 and a second hollow tube 84 extends from boss 80. These respective hollow tubes are dimensioned to seat rods 62 and 64, respectively, in a sliding relationship. As seen in the drawings, the coil springs are positioned around the rod adjacent to and abutting the forward bands and also abut the tubes. The coil springs urge the forward bands away from the rear bands with sufficient, predetermined force so as to distilize the mandibular molars while the rod 70 resists lateral or widening pressure FIGS. 5 through 8 illustrate another embodiment of an orthodontic appliance of the present invention employed to correct malocclusions, particularly Class II overbite, indicated generally by reference number 90, shown in FIG. 1 as mounted in a mold M of the mouth. The appliance 90 includes a maxillary arch expander 92 and a mandibular arch expander 94. The illustrated arch expanders are substantially the same as those illustrated and described in my U.S. Pat. Nos. 5,645,422, 5,769,631, 6,402, 510, and 6,241,517, which are incorporated herein by reference. The maxillary arch expander has a pair of space apart forward bands 96 and 98 with buccal bosses 99 which are attached to the first upper bicuspids B. The maxillary arch expander also includes a pair of rear orthodontic bands 100 and 102 with bosses 103.

Figure 8:
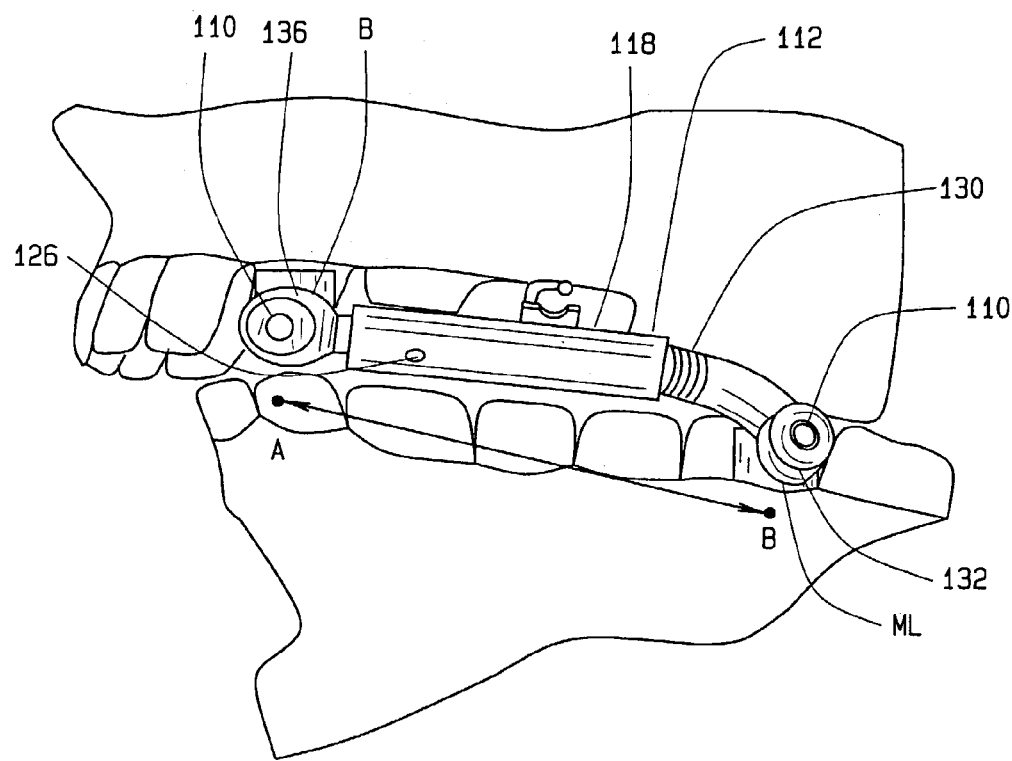
FIG. 8 illustrates a contraction sheath connector of FIG. 7 in use in a first or starting position in the correction of Class II overbite.

The mandibular arch expander 94 includes a pair of rearward orthodontic bands 104 and 106 with buccal bosses 108. The rear orthodontic bands are connected around lower molars ML. The buccal bosses 99 and 108 are adapted to received screws 110 to connect a telescoping connector 112, that is pivotally connected between the upper first bicuspid and the lower molar to correct overbite, as shown in FIG. 8, and will be explained in greater detail below.

Connector 112 is described in detail in my co-pending application Ser. No. 09/975,633, which is incorporated herein by reference. In general, however, connector 112 includes an outer telescoping sheath 114 and a contraction rod 116 slidably engaged in the sheath. The sheath 114 has a first or anterior tube section 118 and a posterior tube section 120. Anterior section 118 has an inner bore 122 with a threaded surface 124. The anterior section 118 includes and opening 126 or other structure for the engagement of a tool to facilitate rotation of the anterior section to effect extension or contraction of the connector.

Posterior tube section 120 has an inner bore 128 that extends the axial length of the section. In the preferred embodiment bore 128 has a threaded surface 130. There is a pivot eyelet 132 on the posterior end of the posterior tube section 120.

As seem in FIG. 8, the eyelet 132 is connected by screw 110 to the band of the mandibular apparatus on the lower molar as described with reference to the maxillary molar in my U.S. Pat. No. 6,036,488, which is incorporated herein by reference. Tube section 120 is designed to fit in bore 122 of anterior section 118 with the threaded surface 130 engaging threaded surface 124. The respective bores 122 and 128 form a contiguous bore of uniform diameter.

Figure 9:
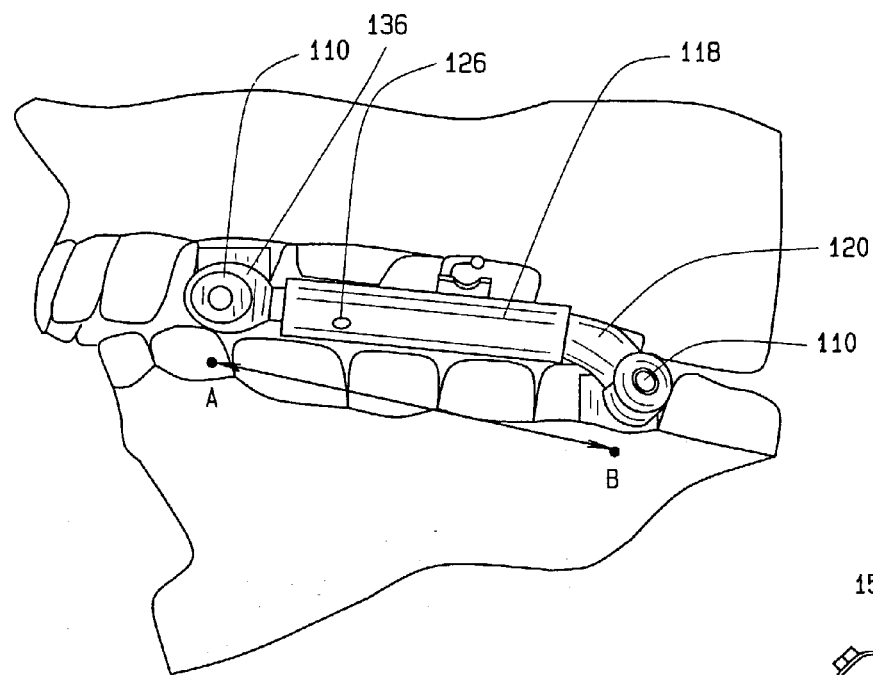
FIG. 9 illustrates a contraction sheath connector of FIG. 7 in use in a second or finished position in the correction of Class II overbite.

Rod 116 has an elongated cylindrical body section 134 with an eyelet 136 at one end for attachment to a maxillary device, as shown in FIGS. 8 and 9, by a pivot screw 110. Rod 116 can be solid or tubular and is sized to slidingly engage in the continuous bore formed by bores 122 and 128. There is a coil spring 138 positioned around body section 134 and secured by insertion into an opening 140 or other appropriate structure or by welding or so forth. In use, the connector 112 is expanded to extend between the maxillary apparatus and the mandibular apparatus, for example, by advancing the anterior tube section 114 by rotation until it fits between the pivotal mounts on the maxillary first bicuspid and the lower molar, as shown in FIG. 8. The spring exerts a contracting force on the rod and, consequently, on the maxillary apparatus. Tension can be increased by advancing the anterior section by rotation around the threads thus stretching the spring to cause more contractive force between points A and B. The contraction sheath can be shortened by reversing the rotation, as shown in FIG. 9. In any event, the contraction force or tension is readily adjusted.

Figure 10:
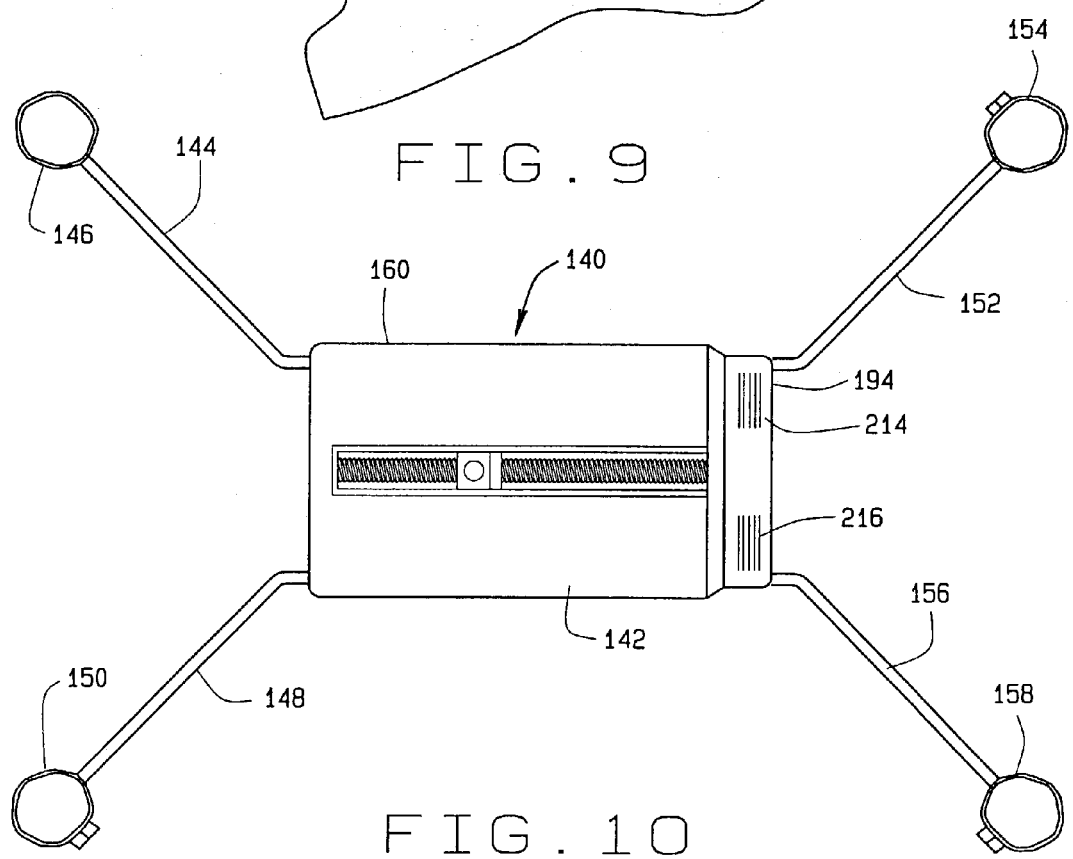
FIG. 10 is a top plan view of another embodiment of a maxillary arch expander of the present invention employing an expansion element connected to orthodontic bands by wires.

FIG. 10 illustrates another embodiment of an orthodontic apparatus generally used to effect maxillary arch expansion, illustrated generally by reference numeral 140. Apparatus 140 includes a substantially centrally disposed expansion element 142, a first forward connecting wire 144 having an orthodontic band 146 at the end, a second forward connecting wire 148 having an orthodontic band 150 at the end, a first rear connecting wire 152 having an orthodontic band 154 at the end, and a second connecting wire 156 also having an orthodontic band 158 at the end. The lengths of the respective wires are dictated by the morphology of the subject's maxilla. The overall size and shape of apparatus 140 can very between subjects. The respective orthodontic bands are of conventional design and can be either integral with the ends of the wires or appropriately attached, as by welding or the like. The components of apparatus 140 can be formed of an appropriate metal, such as Titanium.

Expansion element 142 is constructed and operates as described in my co-pending application Ser. No. 09/975, 633, file Oct. 21, 2001, and which is incorporated herein by reference. The construction and operation of expansion element 142 is also described in reference to FIGS. 11–13, herein. Expansion element 142 includes an outer housing 160 having side walls 162, a top 164, a bottom 166, a back 168 and an open front 170. A channel or groove 172 extends rearwardly from the front edge 170 of the outer housing 160. The groove 172 is defined by sloped walls 174 on opposing sides of the channel. Thus, as seen in FIG. 12, the bottom of the sloped wall 174 is below the inner surface of the rest of the top 164. A triangular shaped rib 176 runs along the center of the inner surface of the bottom 166 between the back 168 and the front 170. A threaded rod 178 extends forwardly from the housing back wall 168 to the front 170. The threaded rod 178 extends along the, center of the housing, and is generally above the rib 176. A pair of posts 182 are disposed on opposite sides of the threaded rod 178, and, like the rod 178, extend forwardly from the back wall 168 to the front wall 170.

An advancing member 184 is slidably received in the housing 160. The member 184 has side walls 186, a bottom 188, a top 190, and a front wall 192. A forward mounting portion 194 extends from the front wall 192. A groove 195 is formed on the outer surface of the bottom 188 and is sized and shaped to slide on the rib 176 of the housing 160. Additionally, a channel 196 having sloped walls 198 is formed in the top 190. The channel 196 is aligned with the housing channel 172, and the sloped walls 198 are complimentarily shaped to the housing's sloped walls 174. Thus, the interaction of the groove 194 with the rib 176 and of the sloped walls 174 and 198 surrounding the channels 172 and 196, respectively, act as keys or guides for the member 184 as it is moved, as will be discussed below.

An internally threaded activation nut 200 is received on the housing's threaded rod 178. The nut 200 is sized such that its peripheral edge is accessible through the channels 172 and 196. The nut 200 includes a plurality of holes 202 in its periphery. The holes 202 are accessible through the channels 172 and 196 using a tool to rotate the nut 200. As can be appreciated, by rotating the nut 200, the nut 200 will move along the rod 178.

An activation wing 204 is mounted in the housing 160 in front of the activation nut 200 to be moved by the nut. The wing 204 includes a central portion 206 which is journaled about the threaded rod 178. The central portion 206 has a central opening sized to prevent the threads of the rod 178 from interfering with movement of the activation wing 204. A pair of arms 208 extends from opposite sides of the central portion 206, and a plate 210 is on the distal end of each arm 208. The plates 210 each have a central hole sized to be received on the posts 182. A spring 212 is journaled around each post 182 between the plates 210 and the front wall 192 of the movable member 184.

As can be appreciated, by rotating the nut 200 such that it moves toward the movable member front wall 192, the activation wing 204 will be moved forwardly, and the springs 212 will be compressed. The springs 212 will thus apply a pressure against the moveable member 184 to cause the housing 160 and the moveable member 184 to move relative to each other, thereby causing expansion of the member 142. Preferably, the moveable member 184 is provided with markings 214, such as millimeter markings so that it can be determined how far the moveable member 184 has been advanced. The markings 214 are preferably provided on the mounting portion 216 of the advancing member 184.

The rib 176 and groove 195 are shown to be triangular, the rib and groove could be any other desired shape. More than one rib and groove could be provided. Additionally, the rib and groove could be reversed, such that the rib is on the advancing member 184 and the groove is on the housing 160.

As can be seen in FIG. 10, the forward wires 144 and 148 with their associated orthodontic bands 146 and 150 are attached to one end of the housing 160. The rear wires 152 and 156 with the respective orthodontic bands 154 and 158 are attached to the forward mounting portion 216 of the advancing member 184. It will be appreciated that when the orthodontic bands are appropriately positioned on the teeth of the maxillary arch as explained in regard to other embodiments above, as the expansion element is expanded, the expansion element will exert arch lengthening force.

Figure 14:
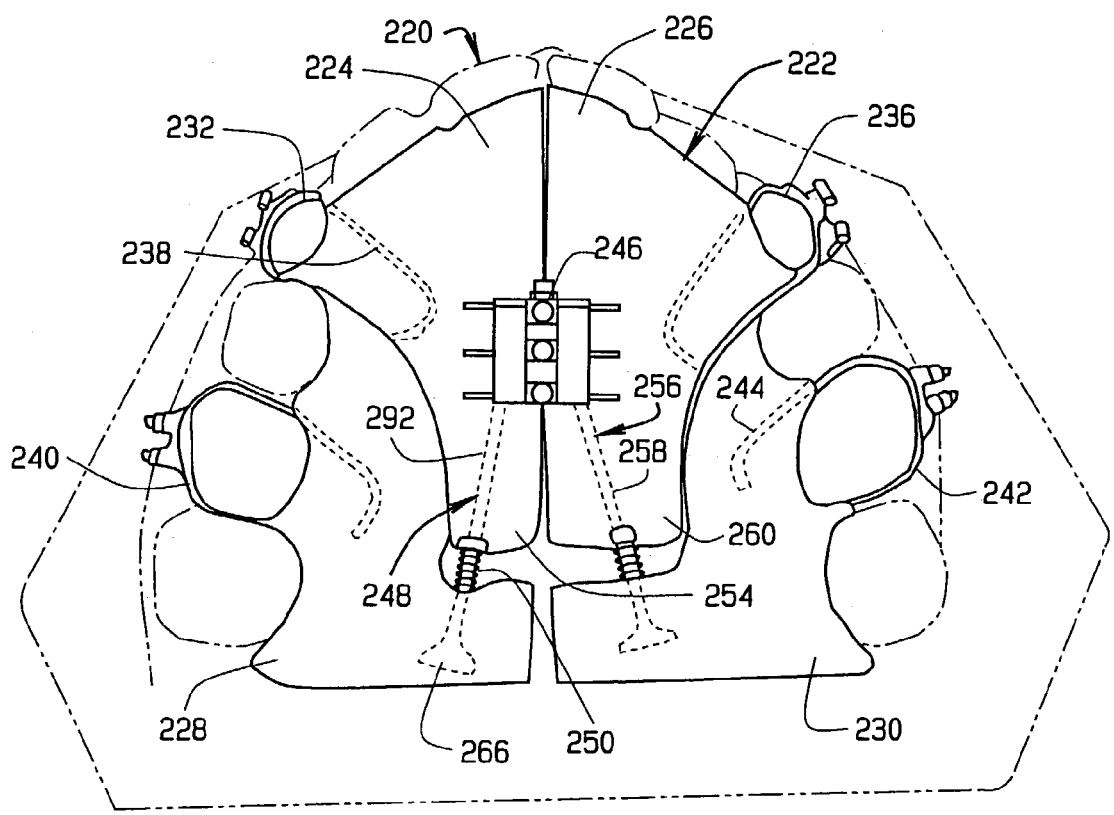
FIG. 14 is a plan view of another embodiment of an orthodontic appliance of the present invention attached to a mold of the maxillary arch.
Figure 15:
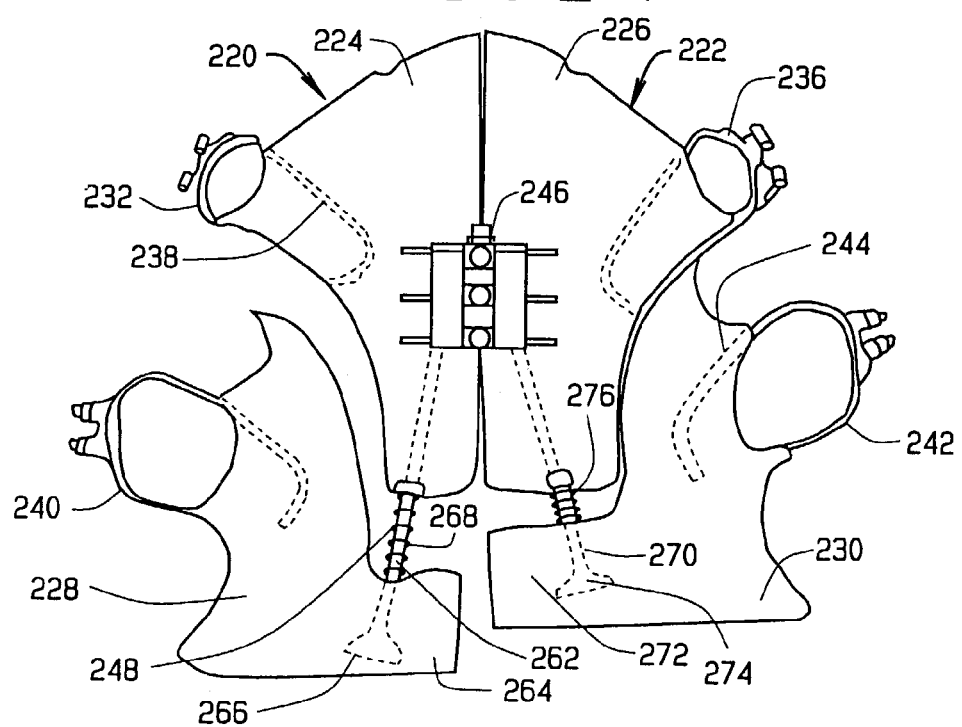
FIG. 15 is another plan view of the orthodontic appliance of FIG. 14, showing its spring forced expansion.

FIGS. 14 and 15 illustrate another embodiment of an orthodontic appliance of the present invention indicated generally by reference numeral 220. Appliance 220 includes a molded palate plate indicated generally by reference numeral 222. Palate plate 222 is molded from an approximate resin material as assumes the shapes of and conforms to the patient's hard palate. Palate plate 222, in the illustrated embodiment, is divided into four quadrants or sections 224, 226, 228, and 230. It will be appreciated that the palate plate 222 is molded and constructed as one piece and then divided into the four sections 224, 226, 228, and 230 by appropriate means. The plate can be divided into only two sections, a forward plate which would include undivided sections 224 and 226 and a rear plate that would comprise undivided sections 228 and 230.

Section 224 includes an orthodontic band 232 attachable to an incisor or canine or the like. Likewise, section 226 includes a similar orthodontic band 236. The orthodontic bands 224 and 226 each include an integral wire or hook 238 which is molded into the palate plate to secure the orthodontic band in place. Correspondingly, sections 228 and 230 include orthodontic bands 240 and 242, respectively. Orthodontic bands 240 and 242 include wires or hooks 244 which are molded into the palate plate to secure the orthodontic band in place. Orthodontic bands 240, 242 are positioned to attach to molars.

Section 224 is connected to section 226 by a jackscrew complex 246, which is a function like the previously described jackscrew complexes. Further, section 224 and 218 are connected by a telescopic rod and tube assembly 248 as can also be seen at 250. Telescopic rod and tube assembly 248 includes a tube 252 molded in a distal tail 254 of section 224. Likewise, section 226 is connected to section 230 with telescopic rod and tube assembly 256. Telescopic rod and tube assembly 256 includes a tube 258 molded in a distal tail 260 of section 236. Section 228 has a rod 262 molded into a lateral section 264. Rod 262 has a transverse section 266 to anchor it in place within the palate plate section and to prevent it from piercing the section under pressure. There is a coil spring 268, preferably constructed from nickel titanium having a predetermined tension around rod 262. Rod 262 seats in tube 252. Section 230 likewise has a rod 270 molded into a lateral section 272. Rod 270 has a transverse section 274 to anchor it in place within the palate plate section and to prevent it from piercing the palate section under pressure. There is a coil spring 276, having a predetermined tension around rod 270. Rod 270 seats upon tube 258.

Appliance 220 can exert both arch widening and arch lengthening forces. Jackscrew complex 246 can be manipulated to exert an appropriate force on the plate sections 222 and 224 to urge them apart and thus effect widening of the arch. Further, telescopic rod and tube assembly 248 can exert a lengthening force between sections 224 and 228 while telescopic rod and tube assembly 256 can exert approximate lengthening force between sections 226 and 230.

It will be understood that if the palate plate is divided into only two sections, a forward and rear plate, then the expansion tubes 248 and 256 would extend between the forward and rear plate. In that embodiment, if the forward plate is not divided, there would not be a jackscrew complex and the device would be employed when there is not desire to effect widening of the arch. Also, other variations my be employed wherein the forward plate is divided into sections 224 and 226 with a jackscrew complex in between, but the rear plate would not be divided into two sections. Consequently, the telescopic rod and tube assembly 248 would extend between section 224 and the rear plate and telescoping rod and tube assembly 256 would extend between section 226 and the rear plate.

Also, it will be understood that the device of the present invention may employ only one plate, a forward or rearward plate. In an embodiment with only a forward plate, which can be divided into two sections, the telescoping rod and tube assembly 248 would exert expansive force between the first forward orthodontic band and the first rear orthodontic band which, absent a rear plate, could be constructed with the tube section directed attached to the rear orthodontic band. The same structures would be employed on the opposite side. Likewise, a pair of forward orthodontic bands, appropriately joined by a laterally extending structure, which could be a straight rod (See, FIG. 1) or an expansion device like a jack screw complex or a laterally extending telescopic rod and tube assembly, would be connected by telescopic rod and tube assemblies to a rear plate, either divided or undivided, to exert lengthening forces between the forward and rear orthodontic bands. The instant design demonstrates exceptional versatility.

It will be appreciated that the described embodiments of the various orthodontic devices of the present invention can be made of any suitable material and in any appropriate dimension without departing from the scope of the appended claims. Therefore, the foregoing description and accompanying drawings should be considered illustrative of preferred embodiments of the best mode of working the invention presently known to the inventor and should not necessarily limit the scope of the claims.

The invention claimed is:

1. An orthodontic arch expansion device, comprising:
   a first forward orthodontic band;
   a second forward orthodontic band;
   a substantially straight connecting member between said first and second forward orthodontic bands;
   a first rear orthodontic band;
   a second rear orthodontic band;
   a first spring loaded expansion apparatus between the first forward orthodontic band and the first rear orthodontic band;
   a second spring loaded expansion apparatus between the second forward orthodontic band and the second rear orthodontic band;
   said first and second expansion apparatuses each having one of a rigid hollow tube and a rigid rod connecting integrally inwardly of the first and second forward orthodontic bands, and said expansion apparatuses further including the other of a hollow tube and rod integrally connecting with the rear orthodontic bands;
   a spring applied to each of the rods, and said rods extending into the hollow tubes, to provide for linear expansion between the forward and rear orthodontic bands to provide the exertion of lengthening forces upon the teeth to which the orthodontic arch expander device is applied.

2. The orthodontic arch expander device of claim 1 wherein the springs of each spring-loaded expansion apparatus are positioned adjacent the forward orthodontic bands to exert lengthening forces on the mandibular arch.

3. The orthodontic arch expander device of claim 1 wherein the springs of each spring-loaded expansion apparatus are positioned adjacent the rear orthodontic bands to exert lengthening forces on the maxillary arch.

4. The orthodontic arch expander device of claim 1 further comprising an acrylic or nance button positioned substantially centrally on the connecting member.

* * * * *